United States Patent
McAuley et al.

(10) Patent No.: US 10,004,864 B2
(45) Date of Patent: Jun. 26, 2018

(54) RESPIRATORY MASK SEALING INTERFACE

(71) Applicant: Fisher & Paykel Healthcare Limited, Auckland (NZ)

(72) Inventors: Alastair Edwin McAuley, Auckland (NZ); Gregory James Olsen, Auckland (NZ); Matthew Roger Stephenson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 393 days.

(21) Appl. No.: 14/740,111

(22) Filed: Jun. 15, 2015

(65) Prior Publication Data

US 2015/0352305 A1 Dec. 10, 2015

Related U.S. Application Data

(63) Continuation of application No. 13/140,385, filed as application No. PCT/NZ2009/000289 on Dec. 16, 2009, now Pat. No. 9,056,178.

(Continued)

(51) Int. Cl.
*A61M 16/06* (2006.01)

(52) U.S. Cl.
CPC ........ *A61M 16/06* (2013.01); *A61M 16/0616* (2014.02); *A61M 16/0622* (2014.02);
(Continued)

(58) Field of Classification Search
CPC .............. A61M 16/06; A61M 16/0605; A61M 16/0611; A61M 16/0616; A61M 16/622; A62B 18/00; A62B 18/02; A62B 18/025
See application file for complete search history.

(56) References Cited

U.S. PATENT DOCUMENTS

| 4,167,185 A | 9/1979 | Lewis |
| 4,739,755 A | 4/1988 | White et al. |

(Continued)

FOREIGN PATENT DOCUMENTS

| EP | 2145645 | 1/2010 |
| WO | WO01/62326 | 8/2001 |

(Continued)

OTHER PUBLICATIONS

International Search Report, International Application No. PCT/NZ2009/000289, dated Mar. 16, 2010; 4 pages.

(Continued)

*Primary Examiner* — (Jackie) Tan-Uyen T Ho
*Assistant Examiner* — Joseph D Boecker
(74) *Attorney, Agent, or Firm* — Knobbe Martens Olson & Bear LLP

(57) ABSTRACT

A sealing interface includes an inner cushion and an outer sheath. The outer sheath substantially seals against the facial contours of the user. The inner cushion and the outer sheath each have a nasal bridge region, left and right cheek regions and either one of an upper lip region or a chin region. In use these regions are aligned with the corresponding nasal bridge region, left and right cheek regions and either the upper lip region or the chin region of a user. The inner cushion includes a hinged region. The hinged region is adapted to flex substantially independently of the inner cushion cheek regions.

22 Claims, 9 Drawing Sheets

Related U.S. Application Data

(60) Provisional application No. 61/138,194, filed on Dec. 17, 2008.

(52) U.S. Cl.
CPC .... *A61M 16/0633* (2014.02); *A61M 16/0666* (2013.01); *A61M 16/0683* (2013.01)

(56) References Cited

U.S. PATENT DOCUMENTS

| | | | |
|---|---|---|---|
| 4,794,921 | A | 1/1989 | Lindkvist |
| 6,892,730 | B2 | 5/2005 | Griffiths |
| 7,237,551 | B2 | 7/2007 | Ho et al. |
| 7,287,528 | B2 | 10/2007 | Ho et al. |
| 7,308,895 | B2 | 12/2007 | Wixey et al. |
| 7,681,575 | B2 * | 3/2010 | Wixey .................. A61M 16/06 128/206.21 |
| 9,056,178 | B2 | 6/2015 | McAuley et al. |
| 2001/0020474 | A1 | 9/2001 | Hecker et al. |
| 2002/0033175 | A1 * | 3/2002 | Bateman ........... A61M 16/0463 128/201.18 |
| 2003/0019495 | A1 | 1/2003 | Palkon et al. |
| 2004/0107968 | A1 | 6/2004 | Griffiths |
| 2005/0257792 | A1 | 11/2005 | Wixey et al. |
| 2008/0006277 | A1 * | 1/2008 | Worboys ............... A61M 16/06 128/207.13 |
| 2008/0110464 | A1 | 5/2008 | Davidson et al. |
| 2009/0000623 | A1 * | 1/2009 | Lynch .................. A61M 16/06 128/206.24 |
| 2009/0107504 | A1 * | 4/2009 | McAuley ............. A61M 16/06 128/205.25 |
| 2010/0018534 | A1 * | 1/2010 | Veliss .................. A61M 16/06 128/206.24 |

FOREIGN PATENT DOCUMENTS

| | | |
|---|---|---|
| WO | WO2004/007010 | 1/2004 |
| WO | WO2004/071565 | 8/2004 |
| WO | WO2005/118040 | 12/2005 |
| WO | WO2006/074513 | 7/2006 |

OTHER PUBLICATIONS

Japanese Examination Report Translation; dated Nov. 18, 2013; 2 pages.

European Search Report, 09833685.2, dated Jul. 4, 2014; 6 pages.

* cited by examiner

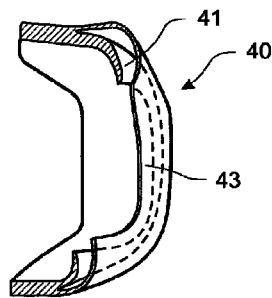
FIGURE 13A
(Prior Art)
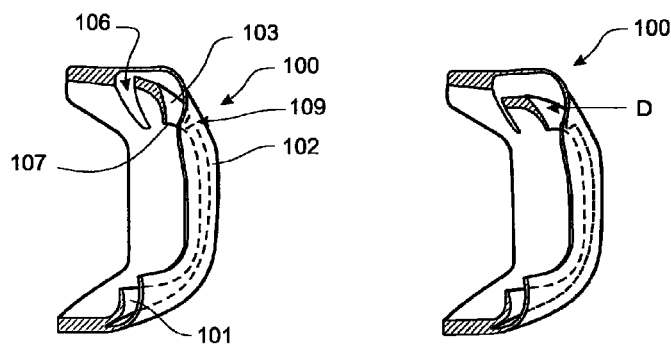
FIGURE 13B     FIGURE 13C
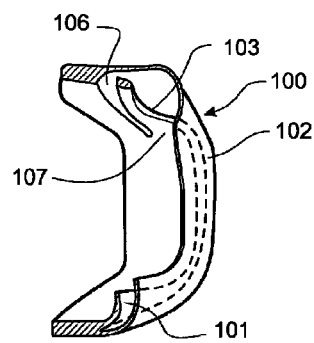     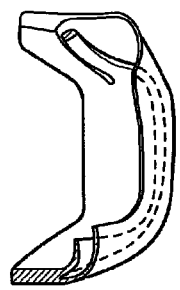
FIGURE 13D     FIGURE 13E

RESPIRATORY MASK SEALING INTERFACE

CROSS-REFERENCE TO RELATED APPLICATIONS

This application is a continuation application of U.S. application Ser. No. 13/140,385, filed on Aug. 16, 2011, which is the national phase of International Application No. PCT/NZ2009/000289, filed Dec. 16, 2009, which claims priority from U.S. Provisional No. 61/138,194, filed Dec. 17, 2008.

BACKGROUND OF THE INVENTION

Field of the Invention

The present invention relates to a patient sealing interface for use as part of an apparatus for supplying a flow of respiratory gases to a user.

Description of the Related Art

It is known to provide a flow of respiratory gases to a user via an interface such as a face mask to relieve a number of ailments—for example sleep apnea or snoring. One problem with supplying a flow of gases to a user via an interface such as a face mask is that it can be difficult to form a good seal between the mask and the face. The mask is often held in place against the user's face by head gear worn on the user's head. In use, the head gear may be over tightened so that the mask is pressed uncomfortably onto the user's face. Alternatively the headgear may be under tightened or applied to the user's head too loosely, preventing the formation of an effective seal between the mask and user's face.

Prior art face masks have attempted to improve the seal between the user's face and the mask and make the sealing interface with the user more comfortable. U.S. Pat. No. 7,308,895 describes a mask assembly having a seal outer sheath and inner cushion. The inner cushion has a raised nasal bridge portion which results in a more flexible seal contact on the bridge of the user's nose. The raised nasal bridge portion is formed by a cut out portion of the inner cushion, the cut-out being on a mask body side of the cushion.

U.S. Pat. No. 6,112,746 describes a nasal mask cushion for sealing a nasal mask to a user's face. The cushion has a first membrane and a second membrane. The second membrane contacts a user's face when in use. The second membrane is thinner than the first membrane and is spaced apart from the first membrane when the mask is not in use. The second membrane is spaced from the first membrane by a greater distance in the nasal bridge region than in the cheek region.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

It is an object of the present invention to provide an improved patient sealing interface, or to at least provide the industry or the public with a useful choice.

In one aspect, the present invention consists in a sealing interface for use as part of an apparatus for supplying a flow of respiratory gases to a user comprising:

an inner cushion, an outer sheath adapted to substantially seal against the facial contours of the user, said inner cushion and said outer sheath each having a nasal bridge region, left and right cheek regions and either one of an upper lip region or a chin region, in use said regions being aligned with the corresponding nasal bridge region, left and right cheek regions and either the upper lip region or the chin region of a user, wherein the inner cushion includes a hinged region, said hinged region adapted to flex substantially independently of said inner cushion cheek regions.

According to a further aspect the hinged region is coupled to each said cheek region by a hinging portion.

According to a further aspect the nasal bridge region is the hinged region.

According to a further aspect the chin region is the hinged region.

According to a further aspect the hinged region is biased towards the outer sheath, in use said inner cushion hinged region substantially contacting said outer sheath.

According to a further aspect in use said sealing interface is coupled with a body that receives said gases, and a gap is provided between the body and the cushion in the hinged region, said gap providing a space for said inner cushion hinged region to flex independently of said cushion cheek regions.

According to a further aspect each said hinging portion is a narrow necked section formed between said inner cushion hinged region and a corresponding said cheek region, said inner cushion hinged region and cheek regions being integrally formed.

According to a further aspect the gap is a valley in the inner cushion nasal bridge region, the valley being in a side of the inner cushion facing said body in use.

According to a further aspect the valley extends the full perimeter of the hinged region, a first end of the valley being adjacent one check region and a second end of the valley being adjacent the other cheek region.

According to a further aspect each narrow necked portion is formed by a notch aligned with a said first or second end of said valley, the notch being formed in a side of the inner cushion facing a user's face in use.

According to a further aspect each narrow necked portion is formed by a slit aligned with a said first or second end of said valley, the slit being formed in a side of the inner cushion facing a user's face in use.

According to a further aspect each said hinging portion biases said inner cushion nasal region towards the outer sheath, in use said inner cushion hinged region substantially contacting said outer sheath.

According to a further aspect said narrow necked section is formed by a first notch formed in a side of the inner cushion that faces the user's face in use, and a second notch formed in the side of the inner cushion that faces the mask body in use, said first and second notches being aligned to form said narrow necked section.

According to a further aspect said narrow necked section is formed by a slit formed in a side of the of the inner cushion that faces the user's face in use, and a notch formed in the side of the inner cushion that faces the mask body in use, said slit and said notch being aligned to form said narrow necked section.

According to a further aspect said narrow necked section is formed by a notch formed in a side of the of the inner cushion that faces the user's face in use.

According to a further aspect said narrow necked section is formed by a notch formed in the side of the inner cushion that faces the mask body in use.

According to a further aspect the hinged region of the cushion flexes, pivots or bends at the hinged portions.

According to a further aspect wherein the hinged region of the cushion flexes, pivots or bends at the hinged portions at a rate of defection, the rate of deflection being 0.04 N/mm±45%.

According to a further aspect the rate of deflection is 0.04 N/mm±30%.

According to a further aspect the rate of deflection is 0.04 N/mm±15%.

According to a further aspect the inner cushion and the outer sheath are separately formed.

According to a further aspect the inner cushion and the outer sheath are integrally formed.

In a further aspect, the present invention consists in a sealing interface for use as part of an apparatus for supplying a flow of respiratory gases to a user comprising:
an inner cushion,
an outer sheath adapted to substantially seal against the facial contours of the user, said inner cushion and said outer sheath each having a nasal bridge region, left and right cheek regions and either one of an upper lip region or a chin region, in use said regions being aligned with the corresponding nasal bridge region, left and right cheek regions and either the upper lip region or the chin region of a user, wherein
said inner cushion nasal bridge region is coupled to each said inner cushion cheek region by a hinging portion so that in use said inner cushion nasal bridge region flexes substantially independently of said inner cushion cheek regions.

In a further aspect, the present invention consists in a sealing interface for use as part of an apparatus for supplying a flow of respiratory gases to a user comprising:
an inner cushion,
an outer sheath adapted to substantially seal against the facial contours of the user, said inner cushion and said outer sheath each having a nasal bridge region, left and right cheek regions and a chin region, in use said regions being aligned with the corresponding nasal bridge region, left and right cheek regions and the chin region of a user, wherein
said inner cushion chin region is coupled to each said inner cushion cheek region by a hinging portion so that in use said inner cushion chin region flexes substantially independently of said inner cushion cheek regions.

In a further aspect, the present invention consists in a patient interface for use as part of an apparatus for supplying a flow of respiratory gases to a user comprising:
a body interface for receiving said gases, and
a sealing interface coupled to said body, said sealing interface adapted to substantially seal against the facial contours of the user, the sealing interface comprising:
an inner cushion and an outer sheath, said inner cushion and said outer sheath each having a nasal bridge region, left and right cheek regions and either one of an upper lip region or a chin region, in use said regions being aligned with the corresponding nasal bridge region, left and right cheek regions and either the upper lip region or the chin region of a user, wherein
the inner cushion includes a hinged region, said hinged region adapted to flex substantially independently of said inner cushion cheek regions.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

Preferred embodiments will be described by way of example only and with reference to the drawings.

FIG. 5b is a side view of the sealing interface inner cushion of FIG. 5a.

FIG. 13a is a prior art sealing interface comprising an integrally formed inner cushion and outer sheath.

FIG. 13b is a sealing interface according to an eighth embodiment.

FIG. 13c is the sealing interface of FIG. 13b showing deflection of the nasal bridge region resulting from the application of a force in the direction of arrow D.

FIG. 13d is a sealing interface according to a ninth embodiment.

FIG. 13e is the sealing interface of FIG. 13d showing the nasal bridge region deflecting substantially independently of the remaining regions of the inner cushion.

DETAILED DESCRIPTION OF THE PREFERRED EMBODIMENT

The sealing interface of the preferred and alternative forms described herein provides improvements in the delivery of CPAP therapy. In particular a sealing interface is described which may allow a reduced pressure of the mask on the user's face and reduces leakage when compared with the prior art. It will be appreciated that the sealing interfaces as described can be used in respiratory care generally or with a ventilator but will be described for illustration with reference to use in a humidified CPAP system. It will also be appreciated that the preferred and alternative forms described can be applied to any form of patient interface including, but not limited to, full face masks sealing around the user's nose and mouth, and nasal masks sealing around the user's nose.

Figure 1:
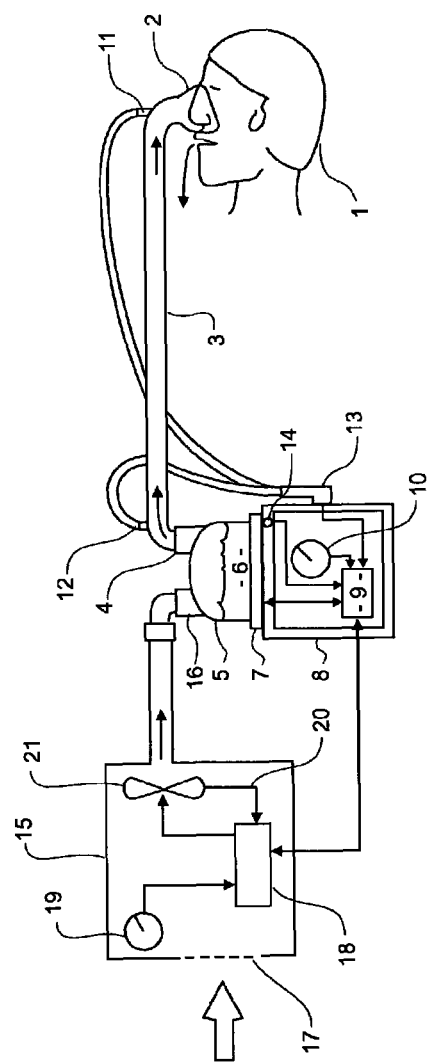
FIG. 1 is a block diagram of a system for providing a heated humidified gases stream to a user such as a continuous positive airway pressure system as might be used in conjunction with the patient sealing interface of the preferred and alternative embodiments.

With reference to FIG. 1 a humidified Continuous Positive Airway Pressure (CPAP) system is shown in which a patient 1 is receiving humidified and pressurised gases through a patient interface 2 connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy.

Inspiratory conduit 3 is connected to the outlet 4 of a humidification chamber 5 which contains a volume of water 6. Inspiratory conduit 3 may contain heating means or heater wires (not shown) which heat the walls of the conduit to reduce condensation of humidified gases within the conduit. Humidification chamber 5 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as a user input interface or dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply or blower 15 which enters the chamber through inlet 16. Exhaled gases from the patient's mouth are passed directly to ambient surroundings in FIG. 1.

Blower 15 is provided with a variable pressure regulator or with a variable speed fan 21 which draws air or other gases through blower inlet 17. The speed of variable speed fan 21 is controlled by electronic controller 18 (or alternatively the function of controller 18 could carried out by controller 9). The controller may control the fan speed or regulated pressure according to any useful criteria. For example the controller may respond to inputs from controller 9 and a user set predetermined required value (preset value) of pressure or fan speed via dial 19.

Patient Interface

Figure 2:
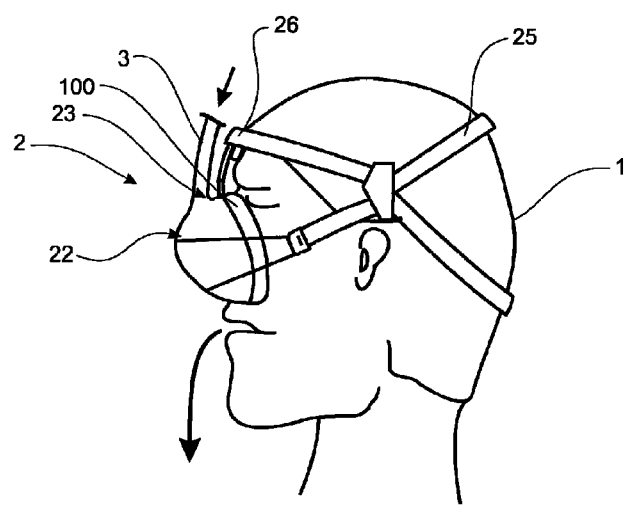
FIG. 2 is a diagram of a nasal mask that may incorporate the sealing interface of the preferred and alternative embodiments.

A typical patient interface in the form of a nasal mask is shown in FIG. 2. The mask includes a hollow body 22 with an inlet 23 connected to the inspiratory conduit 3. The mask 2 is positioned around the nose of the user 1 with the headgear 25 secured around the back of the head of the patient 1. The restraining force from the headgear 25 on the hollow body 22 and the forehead rest 26 ensures enough compressive force on a mask seal 100, to provide an effective seal against the patient's face.

The hollow body 22 is constructed of a relatively inflexible material. For example, the hollow body 22 may be formed from polycarbonate plastic. Such a material would provide the requisite rigidity as well as being transparent and a relatively good insulator. The expiratory gases can be expelled through a valve in the mask, a further expiratory conduit, vent paths through the mask, or any other suitable method.

Mask Seal

The mask seal 100 is provided around the periphery of the mask body 22 to provide an effective seal onto the face of the user to prevent leakage. The mask seal 100 is shaped to approximately follow the contours of a patient's face. The seal is contoured to approximately match the facial contours of a user around the user's nose, from the bridge of the nose, continuing down the cheek regions adjacent each side of the user's nose and across the user's philtrum area. Similarly, if the seal was applied to a full face mask covering a user's nose and mouth, the face seal would be shaped to approximate the facial contours of the user's chin and wider cheek regions. The mask seal 100 will deform when pressure is applied by the headgear 25 to adapt to the individual contours of any particular user.

Figure 3:
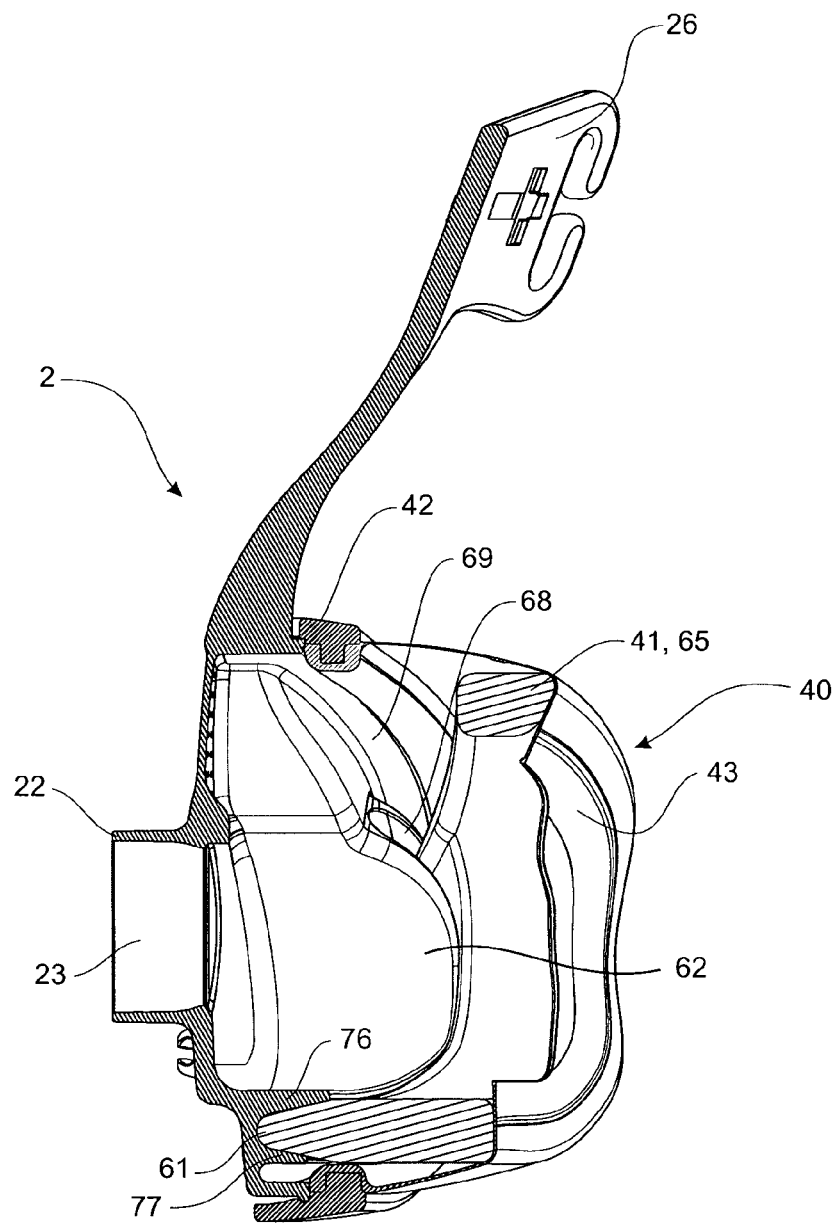
FIG. 3 is a cross sectional view of a face mask that may incorporate the sealing interface of the preferred and alternative embodiments.

A prior art nasal mask assembly for sealing around a user's nose is shown in FIG. 3. The mask seal 40 is composed of an inner cushion 41 covered by an outer sealing sheath 43. The inner cushion 41 is constructed of a resilient material, for example polyurethane foam, to distribute the pressure along the seal around the user's face. In other forms the cushion 41 may be formed of other appropriate material, such as gel, silicone, or other composite materials.

Figure 4A:
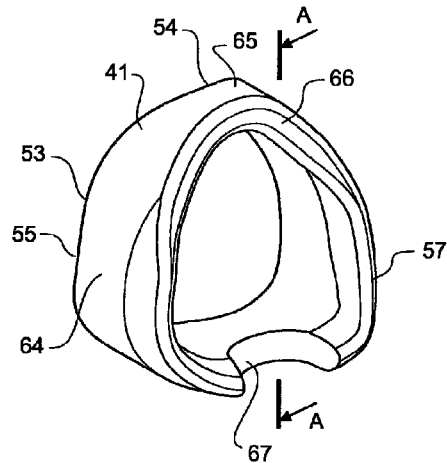
FIG. 4a is a perspective view of a prior sealing interface inner cushion viewed from a mask body side of the inner cushion.
Figure 4B:
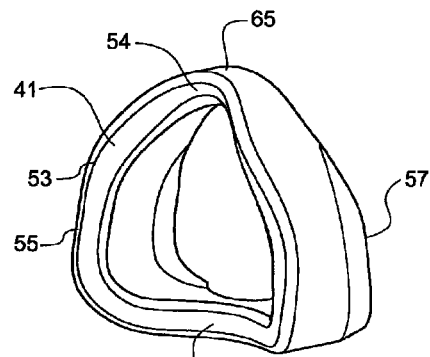
FIG. 4b is a perspective view of the prior sealing interface inner cushion of FIG. 4a viewed from a user's face side of the inner cushion.
Figure 4C:
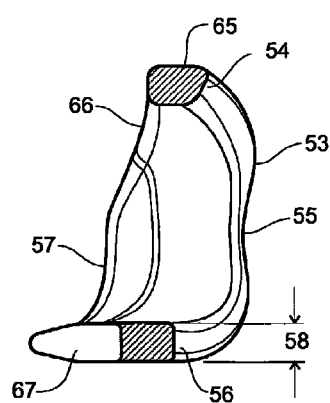
FIG. 4c is a cross sectional view of the prior sealing interface inner cushion of FIG. 4a viewed on arrows A.

A face side 53 of the inner cushion is shaped to approximately match the shape of the user's face. As shown in FIGS. 4a to 4c, there is an indented section 54 intended to fit over the bridge of the patient's nose, a cheek contour 55 on each side to follow the cartilage extending from the middle of the user's nose, and an indented section 56 to seal across the area of the user's face between the user's nose and upper lip. An opposite side of the cushion 57 is shaped to match and interface to the mask body.

The inner cushion may include a raised bridge 65 in the nasal bridge region. The raised bridge 65 can also be described as a cut out or valley 66 formed in the cushion on the mask body side 57 of the cushion. As the raised bridge 65 is unsupported by the mask body 22, it is much more flexible and results in less pressure on the nasal bridge of the patient.

In other forms, the cushion may have other bridge portions, so that in these bridging areas the cushion is more flexible. For example the inner cushion may include a valley 67 formed in the region intended to seal between the nose and upper lip area of a user.

Again with reference to FIG. 3, the inner cushion 41 is located around an inner periphery 61 of an open face 62 of the hollow body 22, contacting the mask body except for in any raised bridge portions such as the raised nasal bridge 65. The cushion is located in a cavity 68 extending around the inner periphery 61 of the body 22, terminating at each side of the raised nasal bridge region 69 of the mask, where the raised bridge portion 65 of the cushion does not contact the mask body 22. The cavity 68 is generally formed by two spaced apart walls 76 and 77 extending around the inner periphery of the mask. The walls are arranged such that the cavity has generally triangular cross section, as shown in FIG. 3.

Similarly the outer sheath 43 is attached to an outer periphery of the mask body 22, either directly to the body 22 in a push fit arrangement (not shown), or indirectly via a relatively inflexible seal clip 42 as shown in FIG. 3. A mask body side of the outer sheath 43 is attached to the seal clip. The seal clip interfaces to the mask body 22. The clip provides a releasable rigid or semi rigid interface, to allow the sealing interface to be easily attached and detached from the mask body many times. The outer sheath 43 surrounds and loosely covers over the top of the inner cushion 41.

One side of the outer sheath is also shaped to match the facial contours of a user's face, and closely matches the shape of the side of the cushion adjacent a user's face in use.

In the prior art mask assembly of FIG. 3, the cushion 41 is a separate item, with the outer sheath 43 fitting in place over the cushion 41. The outer sheath holds the cushion in place within the mask assembly 2. In other forms, the cushion may be permanently or releasably attached to the outer sheath. Alternatively, the cushion may be permanently or releasably attached to the mask body 22, or the outer sheath and inner cushion may be integrally formed. For example, an alternative prior art sealing interface 40 comprising an integrally formed inner cushion 41 and outer sheath 43 is shown in cross section in FIG. 13a. The sealing interface of FIG. 13a is usually integrally formed in silicone.

A sealing interface as described herein may be introduced into a prior art mask, such as the mask of FIG. 3. For example, a sealing interface 100 as described herein could be substituted for the sealing interface 40 of the prior art mask of FIG. 3. The preferred and alternative embodiments will be described in relation to a sealing interface intended to be incorporated into the nasal mask of FIG. 3. However, the sealing arrangement described herein may be incorporated into other mask assemblies, such as full face masks that seal around a user's nose and mouth.

Hinged Region

A sealing interface that includes a mask inner cushion that has a hinged region is described. The hinged region is preferably attached to the inner cushion cheek regions by hinging portions. The hinging portions allow the hinged region of the inner cushion to flex independently of the cheek regions of the cushion. With a hinged region that flexes independently of the remainder of the inner cushion, the force applied by the mask seal interface 100 to a user's face in the hinged region can be independently reduced, without reducing the force applied in other regions of the mask seal.

Hinged Nasal Bridge Region

A common cause for discomfort among users is the pressure applied by the mask seal 100 against the bridge of the user's nose during prolonged use. In extreme cases, prior art sealing interfaces may cause cuts or breakage of the user's skin in the nasal bridge region. A reduction in pressure, or force, applied by the mask sealing interface in the nasal bridge region, while maintaining an effective seal against the user's face, is a significant advantage achieved with the sealing interfaces of the preferred and alternative forms described.

In a preferred embodiment, the nasal bridge region of the inner cushion is the hinged region of the inner cushion. The hinged nasal bridge region is preferably attached or coupled to the inner cushion cheek regions by hinging portions. The hinged nasal bridge region allows the nasal bridge region of the inner cushion to flex independently of the cheek regions and chin or upper lip region of the cushion. With a nasal bridge region that flexes independently of the remainder of the inner cushion, the force applied by the mask seal interface 100 to a user's face in the nasal bridge region can be independently reduced, without reducing the force applied in other regions of the mask seal.

A preferred embodiment of the sealing interface 100 is described with reference to FIGS. 5a to 5c. The inner cushion 101 generally comprises four regions, a nasal bridge region 103 corresponding with the nasal bridge region of a user, two cheek regions 104 corresponding with the left and right cheeks of a user, and an upper lip region 105 corresponding with a user's philtrum area. The nasal bridge region generally extends from the top of a user's nose and down each side of the user's nose to approximately where the sides of the user's nose meets the user's cheeks.

The nasal bridge region 103 is attached to each cheek region 104 by a hinging portion 107. The hinging portions allow the nasal bridge region 103 to flex substantially independently of the remainder of the inner cushion.

Preferably each hinging portion is a narrow necked section 107 formed between the inner cushion nasal region and a corresponding cheek region. Preferably the inner cushion nasal region, cheek regions and chin or upper lip region are integrally formed.

The narrow necked portion 107 allows the nasal bridge region to flex substantially independently of the cheek regions. The raised nasal bridge region bends easily at the narrow necked portions. Any pressure or force applied to the nasal bridge region is effectively isolated from the remaining portions of the inner cushion. In use, the nasal bridge region may bend substantially out of the way of the nasal bridge region of the user's face to provide reduced pressure against the user's nasal bridge, while still providing support to the outer sheath in this area. Support of the outer sheath around substantially the full perimeter of the outer sheath is desirable for creating an effective seal between the mask seal 100 and the user's face. Ideally, a mask seal provides uniform pressure to the user's face around the perimeter of the seal.

The shape of the nasal bridge region differs significantly between users. Where a user has a prominent nose and nasal bridge region, excess pressure is generated in the nasal bridge region of the mask as the mask is tightened to achieve an effective seal in other positions of the seal. A mask seal incorporating a hinged nasal bridge region reduces the pressure in the nasal bridge region for a range of users who suffer from over pressure in the nasal bridge region when using prior art masks.

Figure 5A:
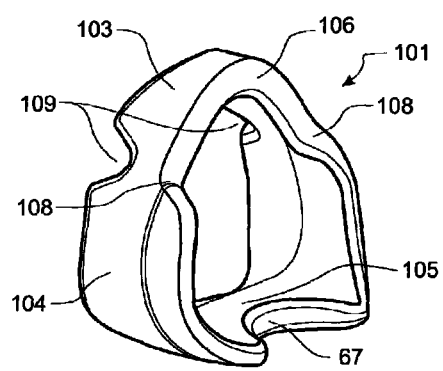
FIG. 5a is a sealing interface inner cushion according to a first embodiment.
Figure 5B:
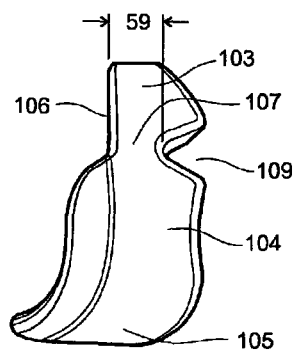
Figure 5C:
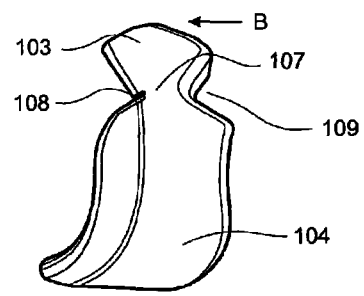
FIG. 5c is the sealing interface inner cushion of FIG. 5a showing deflection of the nasal bridge region resulting from the application of a force in the direction of arrow B.

In the embodiment of FIGS. 5a to 5c, the cushion 101 has a valley 106 on the side of the cushion that in use faces or couples to the mask body 22, the valley being in the nasal bridge region 103 as described with reference to the prior art. Preferably the valley 106 extends substantially the full perimeter of the nasal bridge region, from one cheek region 104 to the other cheek region 104, a first end 108 of the valley 106 being adjacent one check region 104 and a second end 108 of the valley 106 being adjacent the other cheek region 104.

In the embodiment of FIGS. 5a to 5c, each narrow necked portion 107 is formed by a notch 109 formed in the side of the inner cushion that faces the user's face in use, this notch being aligned with an end 108 of the valley 106.

The preferred inner cushion may include other valley or other bridge portions as described with reference to the prior art. For example, the preferred inner cushion has a valley 67 the region of the cushion corresponding with the upper lip region of the user.

FIG. 5c indicates how the nasal bridge region 103 can flex substantially independently of the rest of the inner cushion. With force applied to the apex of the nasal bridge region in the direction of arrow B, notch 109 opens up, and the opposite side of the inner cushion, at an end 108 of the valley 106, compresses. The nasal bridge region of the cushion flexes or bends at the narrow neck section 107, substantially independently of the rest of the inner cushion.

Figure 6:
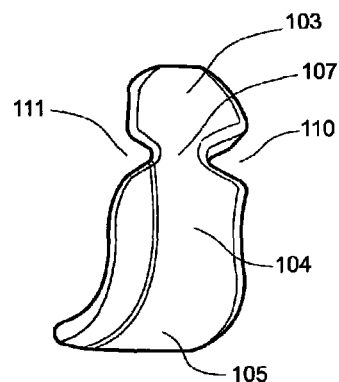
FIG. 6 is a sealing interface inner cushion according to a second embodiment.

As shown in FIG. 6, the narrow necked portion 107 may be formed by a first notch 110 formed in the side of the inner cushion that faces the user's face in use, and a second notch 111 formed in the side of the inner cushion that faces the mask body in use, the first and second notches being aligned to form the narrow necked portion.

Alternatively, the narrow necked portion 107 may be formed by a slit 112 or cut formed in the side of the inner cushion that faces the user's face in use, and a notch 111 formed in the side of the inner cushion that faces the mask body in use, the slit and notch being aligned to form the narrow necked portion.

Figure 7:
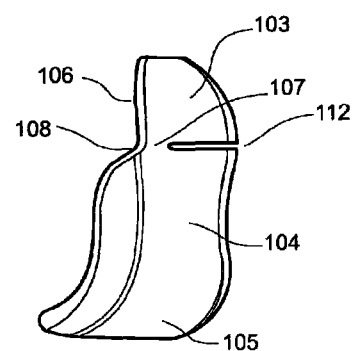
FIG. 7 is a sealing interface inner cushion according to a third embodiment.

Alternatively, as shown in FIG. 7, each narrow necked portion 107 may be formed by a slit 112 formed in the side of the inner cushion that faces the user's face in use, this slit being aligned with an end 108 of the valley 106.

Figure 8:
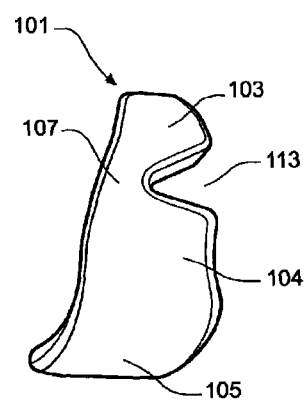
FIG. 8 is a sealing interface inner cushion according to a fourth embodiment.
Figure 9:
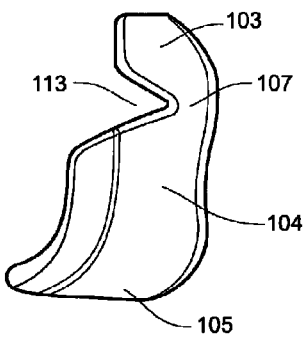
FIG. 9 is a sealing interface inner cushion according to a fifth embodiment.

Alternatively, as shown in FIG. 8, the narrow necked portion 107 may be formed by a notch 113 formed in the side of the inner cushion that faces the user's face in use, the notch extending across a substantial portion of the width of the cushion. Alternatively, as shown in FIG. 9, the narrow necked portion may be formed by a notch 113 formed in the side of the inner cushion that faces the mask body in use, the notch extending across a substantial portion of the width of the cushion. In a further alternative embodiment, the narrow necked portion may be formed by a slit formed in the side of the inner cushion that faces the user's face in use, the slit extending across a substantial portion of the width of the cushion.

One advantage of the embodiment of FIG. 9 is the inner cushion is adapted to provide a continuous contact with the outer sheath around the perimeter of the seal. The notch 110, 113 or slit 112 in the user's face side of the inner cushion in the other embodiments result in a discontinuous contact with the outer sheath which is less desirable.

Figure 10A:
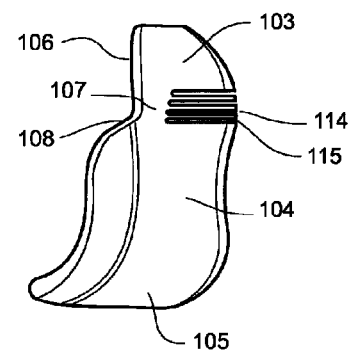
FIG. 10a is a sealing interface inner cushion according to a sixth embodiment.
Figure 10B:
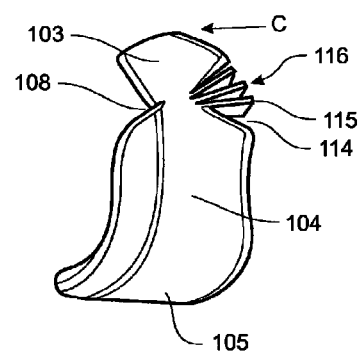
FIG. 10b is the sealing interface inner cushion of FIG. 10a showing deflection of the nasal bridge region resulting from the application of a force in the direction of arrow B.

In the further alternative embodiment of FIG. 10a, a plurality of slits 114 are arranged to create the narrow necked portion 107. In use, as the nasal bridge region of the inner cushion flexes or bends at the hinged portion 107, as shown in FIG. 10b due to a force applied to the apex of the nasal bridge region in the direction of arrow C. The fingers 115 of material between slits 114 provide bridging contact points 116 with the outer sheath to assist with support of the sheath at the narrow necked position of the seal.

The thickness of the cushion around the perimeter of the mask seal is typically around 5 mm, to provide support to the outer sheath in use. The thickness of the cushion is best shown in FIG. 4c as item 58. For a foam cushion with a thickness of around 5 mm, the width 59 of the cushion across the narrow necked portion 107, as indicated in FIG. 5b, is preferably approximately 10 mm. For a width 59 in the narrow necked portion 107 substantially greater than 10 mm, the nasal bridge region 103 will not deflect or bend substantially independently of the remainder of the inner cushion 101. For a width substantially greater than 10 mm, the pressure in the nasal bridge region is not sufficiently reduced when compared to the prior art cushion.

Conversely, for a width 59 in the narrow necked portion 107 substantially less than 10 mm, the nasal bridge region 103 will flex too easily, and will not provide sufficient support to the outer sheath in use. If the narrow necked portion is too narrow, the effectiveness of the seal is compromised as the cushion does not provide sufficient support to the outer sheath in the nasal bridge region.

Preferably the width of the narrow necked portion is in the range of 8 mm-12 mm.

The inner cushion may be made from other materials, such as gel, silicon or other composite materials. For different materials and different perimeter thicknesses, the width 59 of the narrow necked portion may need to change from the preferred dimensions described previously in order to achieve a cushion comprising a nasal bridge region that bends or flexes substantially independently of the remainder of the cushion.

The valley 106 provides a gap or space between the body and the inner cushion into which the nasal bridge region 103 may flex independently of the inner cushion cheek regions. Alternatively, the body may have a cavity or open area in the inner periphery of the mask body 22 into which the nasal region may flex. In this alternative embodiment, the inner cushion may or may not have a valley 106 formed in the nasal bridge region on the side of the cushion that in use faces or couples to the mask body 22. An example of such an embodiment is shown in FIG. 6.

The preferred and alternative forms may also be incorporated into an integrated inner cushion and outer sheath type sealing interface. Examples of an integrated inner cushion and outer sheath type sealing interface 100 are provided in FIGS. 13b and 13d.

In the embodiment of FIG. 13b, each narrow necked portion 107 is formed by a notch 109 formed in the side of the inner cushion 101. Notch 109 is substantially on the side of the inner cushion that faces the user's face in use. A notch or valley 106 is formed in a rearward portion of the inner cushion to provide a space 106 in which the nasal bridge region 103 of the inner cushion can flex into, substantially independently of the remaining regions of the inner cushion 101.

FIG. 13c indicates how the nasal bridge region 103 can flex substantially independently of the rest of the inner cushion. With force applied to the apex of the nasal bridge region in the direction of arrow D, notch 109 opens up, and the opposite side of the inner cushion compresses. The nasal bridge region of the cushion flexes or bends at the narrow neck section 107, substantially independently of the rest of the inner cushion. For clarity, the outer sheath is not shown deformed, however, in use, the outer sheath will deform together with the inner cushion as the inner cushion deflects, the outer sheath maintaining substantial contact with the inner cushion.

A further alternative embodiment is illustrated in FIG. 13d. The narrow necked section is formed by the valley or notch 106 in a rearward portion of the nasal bridge region 103 of the inner cushion 101, without a notch in the forward side of the inner cushion.

Further alternative embodiments are shown incorporated into an integrated inner cushion and outer sheath sealing interface which include arrangements similar to those described previously in relation to a sealing interface comprising a separate inner cushion and outer sheath. For example, the narrow necked portion 107 of FIG. 13b may be formed by a slit instead of notch 109.

In the preferred embodiment, the inner cushion hinged region is biased towards the outer sheath, so that in use the hinged region substantially contacts the outer sheath. In the embodiment of FIGS. 5a to 5c, the nasal region is biased to the sheath contact position because the inner cushion is formed in this shape. The inner cushion nasal bridge region is substantially in contact with the outer sheath when in an un-stressed or un-deflected state. To deflect the nasal bridge region towards the mask body 22, it is necessary to deform the inner cushion nasal bridge region. A high proportion of the stress induced in the inner cushion by a force applied to the nasal bridge region is concentrated in the narrow neck section of the cushion. This achieves deflection of the nasal bridge region substantially independently of the other cushion regions. As a result, the force required to deflect or deform the nasal bridge region is substantially reduced. This provides a more comfortable fit against the user's face compared to prior art mask sealing interfaces, while maintaining an effective seal.

When a force is applied to the nasal bridge region of the inner cushion of the embodiment of FIGS. 5a to 5c, the nasal bridge region twists or bends at the narrow neck sections 107. The narrow neck, or hinging portions 107 bias the inner cushion nasal region towards the outer sheath.

A mask which incorporates the preferred and alternative arrangements as described in this specification provides an improved fit against a range of user's facial contours. The hinged region flexes easily away from, for example, a user's nasal bridge region, while still providing a supporting member for the outer sheath in this region of the seal. In use, gases provided at typical CPAP pressures to the mask interior may cause some inflation of the outer sheath against the user's face. In the sealing interface as described, the outer sheath in contact with the user's face is effectively sandwiched between the inner cushion and the user's face, including in the hinged region of the cushion. This arrangement provides a secure seal against the user's face.

In alternative forms, the sealing interface may be implemented with an inner cushion comprising mechanical hinged portions. For example, the hinged portion may comprise a bracket including two halves connected together via a pivot pin. One bracket half is connected to the hinged region, for example the nasal bridge region, adjacent a cheek region, and the other bracket half is connected to the cheek region adjacent one side of the nasal bridge region. One hinged portion, or both hinged portions may include a biasing mechanism, such as a resilient member, to bias the nasal bridge region to an un-deflected state, as described previously in relation to the preferred embodiment. One or both hinged portions may include an end stop to define the un-deflected state.

Alternatively, a biasing means or resilient member such as a spring may be located in the gap between the raised nasal bridge region and the mask body 22.

In a further alternative form, the hinged region may be separate from the other cushion regions. For example, the nasal bridge region may be pivotally attached to the mask body via two pivot points, the pivot points sharing a common pivot axis, the remaining portions of the inner cushion being attached or coupled to the mask body. Each pivot point may include a pivot pin and a pivot pin receiving portion. One or both pivot points may include a resilient member to bias the inner cushion nasal bridge region to an un-deflected state. In the un-deflected state, the nasal bridge region is substantially in contact with the outer sheath. Alternatively, a biasing means or resilient member such as a spring may be located in the gap between the raised nasal bridge region and the mask body 22, to bias the nasal bridge region of the inner cushion to the un-deflected state.

Figure 11:
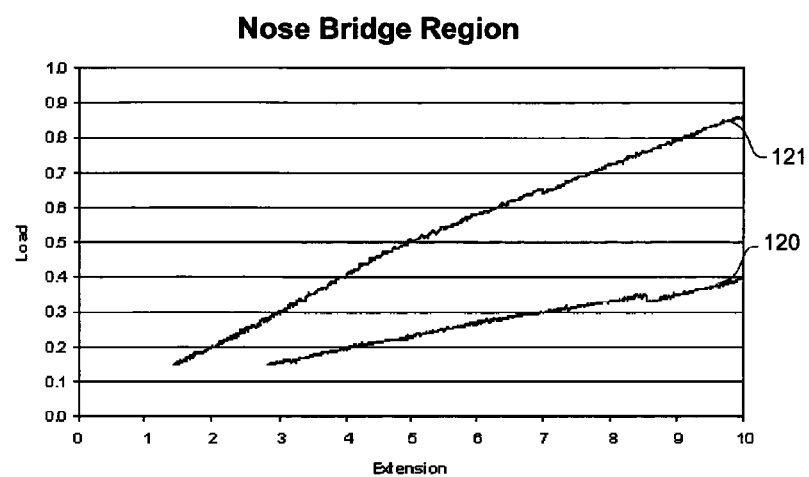
FIG. 11 is a chart showing the force required to deflect the nasal bridge region of the inner cushion of the preferred form compared to the force required to deflect the nasal bridge region of a prior art inner cushion.

A significant reduction in force required to deflect the hinged region of the inner cushion has been achieved with the sealing interface of the preferred and alternative forms as described. For example, FIG. 11 is a chart showing the force (Newton) required to deflect the hinged nasal bridge region of the embodiment of FIGS. 5a to 5c by a distance (mm) compared to the force required to deflect the nasal bridge portion of a prior art seal. FIG. 11 shows that the force 120 required to deflect the nasal bridge region is approximately half the force 121 required to deflect the nasal bridge region of a prior art sealing interface.

The preferred and alternative forms as described herein allow the hinged region of the cushion to flex, pivot or bend about the hinged portions at a preferred rate of defection. For example, where the nasal bridge region of a cushion incorporating the preferred form is the hinged region of the cushion, preferably the hinged nasal bridge region deflects at a rate of 0.04 N/mm±45% when a force is applied to an apex area of the cushion, as indicated by arrow B in FIG. 5C. Preferably the rate of deflection is 0.04 N/mm±30%. Most preferably the rate of deflection is 0.04 N/mm±15%.

Hinged Chin Region

Another problematic area for face or nasal mask sealing interfaces is the chin or upper lip region. For example, the shape of the chin region differs significantly between users. Where a user has a prominent chin, excess pressure is generated in the chin region of the mask seal as the mask is tightened onto the face of a user to achieve an effective seal in other positions of the seal.

Figure 12:
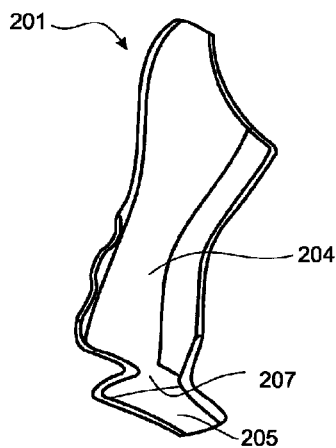
FIG. 12 is a sealing interface inner cushion according to a seventh embodiment.

The preferred and alternative forms may be applied to a mask seal to achieve reduced force or pressure in the chin or upper lip region. As illustrated in FIG. 12, the inner cushion 201 for a full face mask incorporates a hinging portion 207 in the area between the chin region 205 and the cheek region 204. The hinging portion 207, in this example being a narrow necked portion 207, allows the chin region 205 to flex or bend at the hinging portion 207 substantially independently of the remainder of the inner cushion 201. The mask seal reduces the pressure in the chin region for a range of users who suffer from over pressure in the chin region when using prior art masks.

The hinging portion 207 between the chin region 205 and the cheek regions 204 may be formed in the same way as any one of the examples described previously in relation to the hinging portion 107 between the nasal bridge region and the cheek regions. For example, the hinged region 207 may be formed as any one of the narrow necked portion embodiments described previously in relation to the independently flexing nasal bridge region. Alternatively, hinging portion 207 may be a mechanical hinge, the chin region being coupled to the cheek regions by the mechanical hinge. One hinged portion, or both hinged portions may include a biasing means, such as a resilient member, to bias the nasal bridge region to an un-deflected state, as described previously in relation to the hinged nasal bridge region. One or both hinged portions may include an end stop to define the un-deflected state. Alternatively, a biasing means or resilient member such as a spring may be located in a gap between the chin region and the mask body 22.

In a further alternative form, the chin region may be separate from the other cushion regions. The chin region may be pivotally attached to the mask body via two pivot points, the pivot points sharing a common pivot axis, the remaining portions of the inner cushion being attached or coupled to the mask body. Each pivot point may include a pivot pin and a pivot pin receiving portion. One or both pivot points may include a resilient member to bias the inner cushion chin region to an un-deflected state. In the un-deflected state, the chin region is substantially in contact with the outer sheath. Alternatively, a biasing means or resilient member such as a spring may be located in the gap between the chin region and the mask body 22, to bias the chin region of the inner cushion to the un-deflected state.

To allow the chin region to flex, a preferred embodiment includes a valley on the side of the cushion that in use faces or couples to the mask body 22, the valley being in the chin region of the cushion. The valley provides a gap or space between the body and the inner cushion into which the chin region 205 may flex independently of the inner cushion cheek regions 204. Alternatively, the body may have a cavity or open area in the inner periphery of the mask body 22 into which the chin region may flex. In this alternative embodiment, the inner cushion may or may not have a valley formed in the chin region on the side of the cushion that in use faces or couples to the mask body 22.

The foregoing description includes preferred forms thereof. Modifications may be made thereto without departing from the scope of the invention.

What is claimed is:

1. A sealing interface for use as part of an apparatus configured for supplying a flow of respiratory gases to a user, comprising:
    an inner cushion;
    an outer sheath integrally formed with said inner cushion and adapted to contact facial contours of the user, each of said inner cushion and said outer sheath having a nasal bridge region, left and right cheek regions and either one of an upper lip region or a chin region, said nasal bridge region being configured to be aligned with corresponding user nasal bridge region, said left and right cheek regions being configured to be aligned with left and right user cheek regions, and said either one of an upper lip region or a chin region being configured to be aligned with either a user upper lip region or a user chin region of the user in use, respectively;
    wherein said nasal bridge region of said inner cushion is configured to flex relative to said inner cushion left and right cheek regions, said nasal bridge region being coupled to said left and right cheek regions by left and right narrow necked sections formed between said nasal bridge region and a corresponding one of said left and right cheek regions, the left and right narrow necked sections being formed on a side of the inner cushion that faces the user's face in use.

2. The sealing interface as claimed in claim 1, additionally comprising a notch or valley formed in a rearward portion of the inner cushion and extending a full perimeter of the nasal bridge region, a first end of the notch or valley being adjacent one check region and a second end of the notch or valley being adjacent the other cheek region.

3. The sealing interface as claimed in claim 1, wherein said inner cushion nasal region is biased towards the outer sheath, in use said inner cushion nasal bridge region substantially contacting said outer sheath.

4. The sealing interface as claimed in claim 1, wherein the nasal bridge region of the inner cushion flexes, pivots or bends at the narrow necked sections at a rate of deflection being 0.04 N/mm±45%.

5. The sealing interface as claimed in claim 1, wherein the left and right narrow necked sections having a necked section width extending between a first side of the inner cushion that faces the user's face in use and a second side of the inner cushion that is opposite the first side, the necked section width being less than widths of adjacent portions of said nasal bridge region and of said corresponding one of said left and right cheek regions.

6. A sealing interface for use as part of an apparatus for supplying a flow of respiratory gases to a user, comprising:
    an inner cushion;
    an outer sheath integrally formed with the inner cushion, the outer sheath adapted to substantially seal against the facial contours of the user, said inner cushion and said outer sheath shaped to approximately following the contours of a patient's face, each having a nasal bridge region, left and right cheek regions and either one of an upper lip region or a chin region, in use said regions being aligned with the corresponding nasal bridge region, left and right cheek regions and either the upper lip region or the chin region of a user;
    wherein the inner cushion includes a hinged region, said hinged region adapted to flex substantially independently of said inner cushion cheek regions, wherein said hinged region is coupled to each said cheek region by a hinging portion and each said hinging portion is a narrow necked section formed between said hinged region and a corresponding said cheek region, said hinged region and cheek regions being integrally formed, said narrow necked section is formed by a notch or slit formed in a side of the inner cushion that faces the user's face in use, wherein
    said nasal bridge region is the hinged region and the inner cushion has a notch or valley formed in a rearward portion of the inner cushion to provide a space in which the nasal bridge region of the inner cushion can flex into.

7. The sealing interface as claimed in claim 6, wherein the notch or valley formed in a rearward portion of the inner cushion extends the full perimeter of the hinged region, a first end of the notch or valley being adjacent one check region and a second end of the valley being adjacent the other cheek region.

8. The sealing interface as claimed in claim 7, wherein each narrow necked section is formed by a notch or slit formed in the side of the inner cushion facing a user's face in use being aligned with said first or second end of said notch or valley formed in a rearward portion of the inner cushion.

9. The sealing interface as claimed in claim 6, wherein each said hinging portion biases said inner cushion nasal region towards the outer sheath, in use said inner cushion hinged region substantially contacting said outer sheath.

10. The sealing interface as claimed in claim 6, wherein said narrow necked section is formed by a plurality of slits formed in the side of the inner cushion that faces the mask body in use.

11. The sealing interface as claimed in claim 6, wherein the hinged region of the inner cushion flexes, pivots or bends at the hinged portions.

12. The sealing interface as claimed in claim 11, wherein the hinged region of the inner cushion flexes, pivots or bends at the hinged portions at a rate of deflection, the rate of deflection being 0.04 N/mm±45%.

13. The sealing interface as claimed in claim 6, in combination with a patient interface for use as part of an apparatus for supplying a flow of respiratory gases to a user.

14. The sealing interface as claimed in claim 6, wherein said narrow necked section has a necked section width extending between a first side of the inner cushion that faces the user's face in use and a second side of the inner cushion that is opposite the first side, the necked section width being less than widths of adjacent portions of said hinged region and of said corresponding cheek region.

15. A sealing interface for use as part of an apparatus for supplying a flow of respiratory gases to a user, comprising:
an inner cushion,
an outer sheath integrally formed with the inner cushion, the outer sheath adapted to substantially seal against the facial contours of the user, said inner cushion and said outer sheath shaped to approximately following the contours of a patient's face, each having a nasal bridge region, left and right cheek regions and either one of an upper lip region or a chin region, in use said regions being aligned with the corresponding nasal bridge region, left and right cheek regions and either the upper lip region or the chin region of a user, wherein
the inner cushion includes a hinged region, said hinged region adapted to flex substantially independently of said inner cushion cheek regions, wherein
said hinged region is coupled to each said cheek region by a hinging portion, and each said hinging portion is a narrow necked section formed between said hinged region and a corresponding said cheek region, said hinged region and cheek regions being integrally formed, and said nasal bridge region is the hinged region and the inner cushion has a notch or valley formed in a rearward portion of the inner cushion to provide a space in which the nasal bridge region of the inner cushion can flex into, each narrow necked section between the nasal bridge region and each check region formed by the valley or notch in the rearward portion of the nasal bridge region, wherein said narrow necked section is formed by a notch or slit formed in a side of the of the inner cushion that faces the user's face in use.

16. The sealing interface as claimed in claim 15, wherein the notch or valley formed in a rearward portion of the inner cushion extends the full perimeter of the hinged region, a first end of the notch or valley being adjacent one check region and a second end of the valley being adjacent the other cheek region.

17. The sealing interface as claimed in claim 16, wherein each narrow necked section is formed by a notch or slit formed in the side of the inner cushion facing a user's face in use being aligned with said first or second end of said notch or valley formed in a rearward portion of the inner cushion.

18. The sealing interface as claimed in claim 15, wherein each said hinging portion biases said inner cushion nasal region towards the outer sheath, in use said inner cushion hinged region substantially contacting said outer sheath.

19. The sealing interface as claimed in claim 15, wherein said narrow necked section is formed by a plurality of slits formed in a side of the inner cushion that faces a mask body in use.

20. The sealing interface as claimed in claim 19, wherein the hinged region of the inner cushion flexes, pivots or bends at the hinged portions at a rate of deflection, the rate of deflection being 0.04 N/mm±45%.

21. The sealing interface as claimed in claim 15, in combination with a patient interface for use as part of an apparatus for supplying a flow of respiratory gases to a user.

22. A sealing interface as claimed in claim 15, wherein said narrow necked section has a necked section width extending between a first side of the inner cushion that faces the user's face in use and a second side of the inner cushion that is opposite the first side, the necked section width being less than widths of adjacent portions of said hinged region and of said corresponding cheek region.

* * * * *

UNITED STATES PATENT AND TRADEMARK OFFICE
CERTIFICATE OF CORRECTION

PATENT NO. : 10,004,864 B2
APPLICATION NO. : 14/740111
DATED : June 26, 2018
INVENTOR(S) : Alastair Edwin McAuley Page 1 of 1

It is certified that error appears in the above-identified patent and that said Letters Patent is hereby corrected as shown below:

In the Specification

In Column 2, Line 42, change "check region" to --cheek region--

In Column 2, Line 63, change "of the of the" to --of the--

In Column 3, Line 2, change "of the of the" to --of the--

In Column 9, Line 11, change "check region" to --cheek region--

In the Claims

In Column 14, Line 7, Claim 2, change "check region" to --cheek region--

In Column 14, Line 60, Claim 7, change "check region" to --cheek region--

In Column 16, Line 6, Claim 15, change "check region" to --cheek region--

In Column 16, Lines 9-10, Claim 15, change "of the of the" to --of the--

In Column 16, Line 15, Claim 16, change "check region" to --cheek region--

Signed and Sealed this
Twenty-first Day of May, 2019

Andrei Iancu
*Director of the United States Patent and Trademark Office*